United States Patent [19]

Scherkenbeck et al.

[11] Patent Number: 5,365,691
[45] Date of Patent: Nov. 22, 1994

[54] METHODS AND AGENTS FOR COMBATING COCKROACHES

[75] Inventors: Jürgen Scherkenbeck, Leverkusen; Günter Nentwig; Jürgen Lenz, both of Cologne; Jürgen Boeckh, Nittendorf; Gernot Wendler, Erftstadt; Martin Dambach, Burscheid; Bernd-Wieland Krüger, Bergisch Gladbach, all of Germany

[73] Assignee: Bayer Aktiengesellschaft, Leverkusen, Germany

[21] Appl. No.: 207,906

[22] Filed: Mar. 7, 1994

Related U.S. Application Data

[62] Division of Ser. No. 108,100, Aug. 17, 1993, abandoned.

[30] Foreign Application Priority Data

Aug. 24, 1992 [DE] Germany .................... 4228002

[51] Int. Cl.$^5$ ............... A01M 1/10; A01M 1/14; A01N 25/00; C07C 31/125
[52] U.S. Cl. ..................... 43/114; 43/121; 424/84; 568/840; 585/16
[58] Field of Search ............ 424/84; 43/114, 121

[56] References Cited

U.S. PATENT DOCUMENTS

| | | | |
|---|---|---|---|
| 3,072,526 | 1/1963 | Butenandt et al. | 424/84 |
| 3,127,439 | 3/1964 | Sims | 568/840 |
| 3,127,440 | 3/1964 | Sims | 568/840 |
| 3,239,566 | 3/1966 | Slaugh et al. | 568/840 |
| 3,241,908 | 3/1966 | Mazur et al. | 568/840 |
| 3,282,974 | 11/1966 | Bruno et al. | 568/840 |
| 3,513,084 | 5/1970 | Breton et al. | 568/840 |
| 4,044,495 | 8/1977 | Nishimura et al. | 43/114 |
| 4,851,218 | 7/1989 | Hildebrandt et al. | 424/84 |
| 4,853,217 | 8/1989 | Francke | 428/84 |
| 5,053,223 | 10/1991 | Krieg et al. | 424/84 |
| 5,063,058 | 11/1991 | Chuman et al. | 424/84 |
| 5,072,057 | 12/1991 | Oswald et al. | 568/840 |
| 5,126,128 | 6/1992 | Mori et al. | 424/84 |

FOREIGN PATENT DOCUMENTS

54333  3/1988  Japan .................. 568/840

OTHER PUBLICATIONS

Jones "J. Chem. Soc" (c) No. 22 (1968).
Chemical Abstracts; 5–Agrochemicals, vol. 118, No. 15, 1993, p. 289; 141790z: A. Tai et al, "Synthesis and Field Test of a Pheromone Mimic of the Pine Sawfly".
Chemical Abstracts; 12–Nonmammalian Biochm., vol. 107, No. 5, 1987, p. 437; 36894m: M. Augustynowicz et al, "Cuticular Hydrocarbons of the German Cockroach".
Chemical Abstracts, vol. 105, No. 25, 1986, p. 482; 223086v: K. Lockey et al., "Cuticular Methylakanes of Adult Cockroaches, . . . ".
Chemical Abstracts; 12–Nonmammalian Biochem., vol. 76, No. 19, 1972, p. 265; 110556m: L. Jackson et al, "Cuticular Lipids of Insects . . . ".
Chemical Abstracts, 9–Nonmammalian Biochemistry, vol. 72, No. 19, p. 103; 97733p: L. Jackson et al, "Cuticular Lipids of Insects . . . "; 1970.
Chemical Abstracts; 9–Nonmammalian Biochemistry, vol. 72, No. 19, 1970, p. 103; 97732n: K. Tartivita, "Cuticular Lipids of Insects . . . ".
Database WPI, Week 7912, Derwent Publications, Feb. 1979, AN 79-23097B & JP54020868-A, Earth Seiyaku KK (European Patent Office).
DatabaseWPI, Week 7736, Derwent Publications, AN 77-64270Y & JP52031416-B, Yamabun Yuka KK (European Patent Office); Aug. 1977.
Database WPI, Week 6800, Derwent Publications, AN 67-06393H & JP44011920-B, Sankyo Co. Ltd. (European Patent Office). 1967.
Chemical Abstracts, 1977–1981–Chemical Substance Index, Seite 37007CS, 2 pages. (10th Collective).
Chemical Abstracts, 1987–1991 Chemical Substance Index, Seite 63753CS, 2 pages. (12th Collective).
Tetrahedron, vol. 48, No. 15, pp. 3139-3146, 1992; E. Hedenstrom et al, "Sex Pheromone of Pine Sawflies. Chiral Syntheses of some Active . . . ".

Primary Examiner—Joseph E. Evans
Attorney, Agent, or Firm—Sprung Horn Kramer & Woods

[57] ABSTRACT

The present invention relates to the use of compounds of the general formula I $$CH_3-(CH_2)_m-\underset{R^2}{\underset{|}{CH}}-R^1 \qquad I$$

in which $R^1$ represents $C_1$–$C_5$-alkyl or hydroxy-$C_1$–$C_5$-alkyl;
$R^2$ represents $C_1$–$C_5$-alkyl; and
m represents an integer from 10 to 20,
for combating cockroaches.

10 Claims, No Drawings

METHODS AND AGENTS FOR COMBATING COCKROACHES

This application is a divisional of application Ser. No. 08/108,100, filed Aug. 17, 1993, now abandoned.

The present invention relates to the new use of certain chemical compounds of attractants for combating cockroaches, agents for combating cockroaches comprising these compounds, and new attractants and a process for their preparation.

Infestation with cockroaches is a considerable hygiene problem on domestic and trading premises, which requires combating of the cockroaches. Due to their habits, however, cockroaches are difficult to combat. A particular problem is concentrating the cockroaches around mechanical devices for combating them (traps) or insecticidally active agents. To this end, the sexual pheromones of the American cockroach (*Periplanata americana*) have already been employed (cf. Bell 1986, Pesticide Control N. 12), but their specificity and efficacy have not always led to satisfactory results.

It has now been found that the compounds of the general formula I

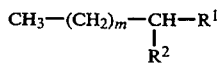

in which
$R^1$ represents $C_1$-$C_5$-alkyl or hydroxy-$C_1$-$C_5$-alkyl;
$R^2$ represents $C_1$-$C_5$-alkyl; and
m represents an integer from 10 to 20,
can be employed particularly advantageously for combating cockroaches.

The compounds of the general formula I have an attractant effect on cockroaches and are suitable for concentrating the cockroaches in particular locations where they can be combated by mechanical and/or chemical means. The compounds of the formula I are highly active, stable and readily accessible by synthesis. The compounds of the general formula I can be employed as individual compounds or in the form of mixtures with each other.

In the above general formula and in the general formulae and definitions of radicals mentioned below, alkyl as such or as a component of a different radical represents straight-chain or branched (preferably straight-chain) alkyl having 1 to 5, preferably 1 to 4 and particularly preferably 1 to 3, carbon atoms, with methyl, ethyl, n- and i-propyl and n-, i-, s- and t-butyl being mentioned specifically.

$R^1$ preferably represents $C_1$-$C_4$-alkyl or hydroxy-$C_1$-$C_4$-alkyl.
$R^2$ preferably represents $C_1$-$C_3$-alkyl.
m preferably represents an integer from 11 to 19.

Compounds of the general formula I which are preferably used according to the invention are those which represent a combination of these meanings which have been mentioned above as being preferred.

$R^1$ particularly preferably represents $C_1$-$C_3$-alkyl or hydroxy-$C_1$-$C_3$-alkyl (preferably 1-hydroxy-$C_1$-$C_3$-alkyl),
$R^2$ particularly preferably represents methyl or ethyl.
m particularly preferably represents an integer from 12 to 18.

Compounds of the general formula I which are particularly preferably used according to the invention are those which represent a combination of these meanings which have been mentioned above as being particularly preferred.

$R^1$ very particularly preferably represents methyl, ethyl (preferably ethyl) or hydroxyethyl (preferably 1-hydroxyethyl).
$R^2$ very particularly preferably represents methyl.
m very particularly preferably represents an integer from 13 to 17.

Compounds of the general formula I which are very particularly preferably used according to the invention are those which represent a combination of these meanings which have been mentioned above as being very particularly preferred.

Examples of compounds of the formula I which can be used particularly advantageously according to the invention can be seen from Table 1 below:

TABLE 1

| Compound No. | Formula |
|---|---|
| 1 | $H_3C$—$(CH_2)_{17}$—$\underset{\underset{CH_3}{\|}}{CH}$—$\underset{\underset{OH}{\|}}{CH}$—$CH_3$ |
| 2 | $H_3C$—$(CH_2)_{13}$—$\underset{\underset{CH_3}{\|}}{CH}$—$\underset{\underset{OH}{\|}}{CH}$—$CH_3$ |
| 3 | $H_3C$—$(CH_2)_{13}$—$\underset{\underset{CH_3}{\|}}{CH}$—$CH_2$—$CH_3$ |
| 4 | $H_3C$—$(CH_2)_{17}$—$\underset{\underset{CH_3}{\|}}{CH}$—$CH_2$—$CH_3$ |
| 5 | $H_3C$—$(CH_2)_{15}$—$CH$—$\underset{\underset{CH_3}{\|}}{CH}$—$CH_2$—$CH_3$ |
| 6 | $H_3C$—$(CH_2)_{19}$—$\underset{\underset{CH_3}{\|}}{CH}$—$CH_2$—$CH_3$ |
| 7 | $H_3C$—$(CH_2)_{13}$—$\underset{\underset{CH_3}{\|}}{CH}$—$CH_3$ |
| 8 | $H_3C$—$(CH_2)_{15}$—$\underset{\underset{CH_3}{\|}}{CH}$—$CH_3$ |
| 9 | $H_3C$—$(CH_2)_{17}$—$\underset{\underset{CH_3}{\|}}{CH}$—$CH_3$ |
| 10 | $H_3C$—$(CH_2)_{13}$—$\underset{\underset{CH_3}{\|}}{CH}$—$(CH_2)_2$—$CH_3$ |
| 11 | $H_3C$—$(CH_2)_{13}$—$\underset{\underset{CH_2CH_3}{\|}}{CH}$—$CH_2$—$CH_3$ |
| 12 | $CH_3$—$(CH_2)_{13}$—$\underset{\underset{CH_3}{\|}}{CH}$—$(CH_2)_3$—$CH_3$ |
| 13 | $CH_3$—$(CH_2)_{13}$—$\underset{\underset{\underset{CH_3}{\|}}{CH_2}}{\underset{\|}{CH}}$—$CH_2$—$CH_3$ |

Some of the compounds of the general formula I are known (cf., for example, An. Bromatol. 30, 267 (1979); insect Biochem. 13, 381 (1983); J. Chem. Ecol. 6,309 (1980); An. Bromatol. 31 137 (1979); Biochem. Syst.

Ecol. 16, 647 (1988); Riv. ital. Sostanze Grasse 63, 213 (1986); J. Chem. Ecol. 15, 939 (1989)) and can be obtained by known processes and methods (cf., for example, Org. Reactions 4, 378 (1948); Chem. Rev. 65, 63 (1965). Many of the compounds of the general formula I can also be prepared by the process described below.

The compounds of the general formula I in which
$R^1$ represents hydroxy-$C_1$-$C_5$-alkyl (preferably α-hydroxy-$C_1$-$C_5$-alkyl);
$R^2$ represents $C_1$-$C_5$-alkyl; and
m represents an integer from 10 to 20,
are new and part of the present invention.

Preferred definitions and combinations of radicals for these new compounds are the definitions of radicals and combinations of radicals whose preferred ranges have been illustrated above.

In the very particularly preferred new compounds,
$R^1$ represents —CHOH—$CH_3$;
$R^2$ represents methyl and
m represents an integer from 13 to 17.

The new compounds of the general formula I can be prepared by the following process, which is also part of the present invention. The new compounds are obtained by reacting
ketones of the general formula II

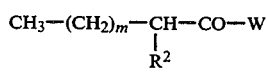

in which
$R^2$ and m have the abovementioned meaning and
W represents $C_1$-$C_4$-alkyl,
with a reducing agent in the presence of a diluent.

If, for example, 3-methyl-heptadecan-2-one is used as starting materials in the process according to the invention, then the course of the reaction can be illustrated by the following equation:

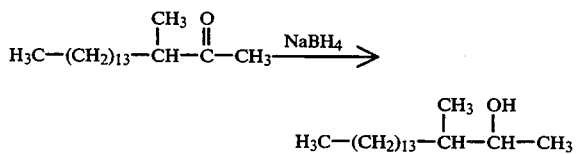

The ketones of the general formula II to be used as starting materials in the process according to the invention are known or can be prepared by known processes and methods (cf. Agr. Biol. Chem. 40, 391 (1976); J. Org. Chem. 40, 3456 (1975); J. Org. Chem. 40, 2410 (1975)).

The abovementioned general definitions of radicals or illustrations, or the definitions of radicals or illustrations whose preferred ranges have been mentioned above, can be combined with each other as desired, that is to say that combinations between the particular preferred ranges are also possible. They apply to the end products and analogously to the precursors and intermediates.

The process according to the invention is preferably carried out in the presence of a diluent. Diluents which are preferably used are polar solvents such as ethanol, propanol, dioxane, dimethyl sulphoxide and dimethylformamide and mixtures of these. Lower alkyl alcohols such as ethanol and propanol are particularly preferred.

Reducing agents are employed in the processes according to the invention. Examples of reducing agents are lithium borohydride, sodium borohydride and lithium alanate, as well as hydrogen in the presence of customary hydrogenation catalysts such as $PtO_2$ or Raney nickel. Sodium borohydride is particularly preferred.

When carrying out the process according to the invention, the reaction temperatures can be varied within a substantial range. The process is preferably carried out at temperatures between −20° C. and +80° C., particularly preferably at temperatures between 0° C. and 40° C.

To carry out the process according to the invention, between 1 and 3 moles, particularly preferably 1 mole, of reducing agent is preferably employed per mole of starting compound of the formula II. The reactants are preferably combined at approximately 0° C. and the mixture is stirred at a slightly elevated temperature until the reaction has ended.

Work-up can be carried out by customary methods; for example by concentrating the reaction mixture, taking up the residue in water and cyclohexane, extracting the mixture using cyclohexane, reconcentrating the extract and purifying the crude product by column chromatography.

The compounds of the general formula I (especially the new compounds) can be employed according to the invention for combating cockroaches, that is to say insects from the order of the Blattodea, in particular of the family Blattellidae, preferably of the species *Blattella germanica* or of the family Blattidae, preferably of the species *Blatta orientalis* and *Periplaneta americana*, but also against other species of cockroaches, but very particularly preferably against *Blatella germanica*.

The compounds of the general formula I affect the behaviour of the cockroaches in such a way that they can be found in greater numbers, or migrate to, those locations which have been treated with compounds of the general formula I, or which contain such compounds. Thus, the compounds of the general formula I are powerful attractants. Thus, the compounds of the formula I can be employed, quite generally, for combating cockroaches, independently of the nature of the method used. By way of example and preferably, they can be employed in mechanical methods in cockroach traps or devices which use adhesives, or they can be employed in biological or chemical methods or in a combination of such methods. In mechanical devices, the compounds of the formula I can be applied over the entire device or large areas thereof or to suitable discreet locations, for example by painting, spraying on, impregnating, printing on, if appropriate in conjunction with other active agents such as attracting colours, bait materials or other attractants, insecticides and the like. In biological or chemical methods, the compounds of the formula I can exist in the form of a mixture with the entomopathogenic organisms (for example viruses or microorganisms) or with the natural or synthetic insecticides, or they can be placed in sufficiently close vicinity to these organisms or substances. The same applies analogously to a combination of a plurality of methods.

The compounds of the general formula I can be used as individual compounds or in the form of a mixture with each other.

A person skilled in the art will be readily capable of determining the compounds, application methods and amounts which are favourable for the particular purposes on the basis of simple calculations or simple experiments.

The compounds of the general formula I are preferably incorporated into an insecticide-containing bait or into adhesive traps, or applied in the vicinity of the bait material (for example above it). The compounds of the general formula I can also exist in a form in which they are released over a prolonged period (slow-release formulations). To this end, they can be incorporated, for example, into polymer material, paraffins, waxes and the like or exist in microencapsulated form. Traps which can be used are the customary devices, and bait materials which can be used are customary agents which attract the cockroaches because they are palatable. The compounds of the general formula I are preferably employed in amounts of 0.0001 to 20 mg (very particularly preferably 0.01 to 0.1 mg) per bait or trap, for example adhesive trap.

The compounds can also be applied in the form of the customary sprays, if appropriate as a mixture with suitable insecticides. To this end, the customary formulations (for example also microencapsulation) can be used, and they can be applied using the application devices which are conventionally used. Equally, it is possible to formulate the compounds of the general formula I, if appropriate in the form of a mixture with suitable insecticides, to give dusts or granules which can be scattered. The application rates of the compounds of the general formula I are preferably 1 to 500 mg per m² and particularly preferably 2 to 200 mg per m². Using the compounds of the general formula I allows the effectiveness of mechanical devices (such as traps, adhesive tapes) and, in particular, also of insecticidal agents to be improved to a considerable extent. The present invention therefore also relates to mechanical devices for combating cockroaches and agents which contain at least one compound of the general formula I. Preferred mechanical devices and agents are the customary cockroach traps which contain, if appropriate, baits, other attractants or edible substances and/or insecticidal substances, as well as agents and traps which have a tacky surface to which the cockroaches adhere and which, if appropriate, contain edible substances and attractants and/or insecticidally active substances of at least one compound of the general formula I, besides customary carriers and auxiliaries. In this case, the compounds of the general formula I can be part of the tacky surface or they can exist in the immediate vicinity of the latter. In mechanical devices, it is also possible to employ combinations of traps and agents having a tacky surface.

Another part of the present invention are agents for combating cockroaches which contain at least one compound of the general formula I and at least one insecticidally active substance, if appropriate besides customary carriers and auxiliaries and/or other additives (such as baits, attractants), it being possible for the compounds of the formula I to be in the form of a mixture with the remaining components or to be arranged separately. These agents can also contain entomopathogenic viruses or microorganisms which are active against cockroaches, either additionally or instead of the insecticidally active substances.

Substances which can used as insecticidal substances are all those which are active against cockroaches, since there is no undesirable interaction between the insecticidally active substances and the compounds of the general formula.

Insecticidally active substances can be, for example, from amongst the insecticidally active phosphoric esters, carbamates, the natural and synthetic pyrethroids, nitroimino, nitromethylene, cyanoimino or cyanomethylene compounds, pyrrolidine-2,4-dione derivatives and/or pyrazoline derivatives.

The following may be mentioned as insecticidal substances which are particularly preferred according to the invention:

1) carbamic esters of the formula III

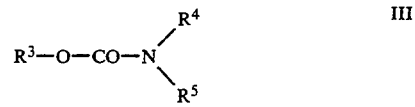

in which
R³ represents an optionally substituted carbocyclic or heterocyclic aromatic radical or an optionally substituted oxime radical (the radicals R³ which are illustrated further below being preferred),
R⁴ represents $C_1$–$C_4$-alkyl and
R⁵ represents hydrogen, $C_1$–$C_4$-alkyl or a radical u, where
u represents the radical —CO—R⁶ in which
R⁶ represents halogen, $C_1$–$C_4$-alkyl, $C_1$–$C_4$-alkoxy, $C_3$–$C_5$-alkenoxy, $C_3$–$C_5$-alkinoxy, $C_1$–$C_4$-alkylthio, $C_1$–$C_4$-alkyl-amino, Di-$C_1$–$C_4$-alkylamino, $C_1$–$C_4$-alkylhydroxylamino,
or represents phenoxy, phenylthio or phenylamino, each of which is optionally substituted by halogen, nitro, cyano, trifluoromethyl, $C_1$–$C_4$-alkyl, $C_1$–$C_4$-alkoxy, $C_1$–$C_4$-alkylenedioxy, $C_1$–$C_4$-alkylthio, $C_1$–$C_4$-alkoxy-carbonyl, or represents 2,3-dihydro-2,2-dimethyl-7-benzofuranyl, or the radical

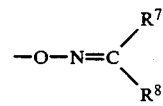

in which
R⁷ represents hydrogen, $C_1$–$C_4$-alkyl or Di-$C_1$–$C_4$-alkylamino-carbonyl and
R⁸ represents $C_1$–$C_4$-alkyl, $C_1$–$C_4$-alkylthio, cyano-$C_1$–$C_4$-alkylthio, $C_1$–$C_4$-alkylthio-$C_1$–$C_4$-alkyl, or the two radicals R⁷ and R⁸ together represent $C_2$–$C_8$-alkanediyl which is optionally interrupted by oxygen, sulphur, SO or $SO_2$, or
in which
u represents the radical —$S_q(O)_r$—R⁹, in which
q represents 1 or 2 and
r represents 0, 1 or 2, where, in the event that q represents 2, r represents 0 and
R⁹ represents $C_1$–$C_4$-alkyl, $C_3$–$C_5$-alkenyl, $C_3$–$C_5$-alkinyl or $C_3$–$C_6$-cycloalkyl, each of which is optionally substituted by halogen, or represents phenyl, benzyl or phenylethyl, each of which is optionally substituted by halogen, cyano, nitro, trifluoromethyl, trifluoromethoxy, trifluoromethylthio, $C_1$–$C_{14}$-alkyl or $C_1$–$C_4$-alkoxy or represents the radical

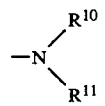

in which
R10 represents $C_1$–$C_4$-alkyl, $C_3$–$C_5$-alkenyl, $C_3$–$C_5$-alkinyl, $C_3$–$C_6$-cycloakyl or benzyl and $R^{11}$ represents $C_1$–$C_4$-alkyl, $C_3$–$C_5$-alkenyl, $C_3$–$C_5$-alkinyl, $C_3$–$C_6$-cycloalkyl, benzyl, phenylethyl, halogencarbonyl, formyl, $C_1$–$C_4$-alkyl-carbonyl, $C_1$–$C_4$-alkoxy-carbonyl, $C_1$–$C_4$-alkoxyphenoxy-carbonyl, $C_3$–$C_5$-alkinoxy-carbonyl, $C_3$–$C_5$-alkenoxycarbonyl, $C_1$–$C_4$-alkylthiocarbonyl, $C_1$–$C_4$-alkyl-amino-carbonyl, $C_1$–$C_4$-alkylhydroxylamino-carbonyl, $C_1$–$C_{10}$-alkyl-phenoxycarbonyl, di-$C_1$–$C_4$-alkyl-aminocarbonyl, phenylthiocarbonyl, phenoxycarbonyl, 2,3-dihydro-2,2-dimethyl-7-benzofuranyloxycarbonyl, or represents phenylsulphenyl, phenylsulphinyl, phenylsulphonyl or phenyl, each of which is optionally substituted by halogen, cyano, nitro, trifluoromethyl, $C_1$–$C_{10}$-alkyl or $C_{1-4}$-alkoxy, or represents the radical

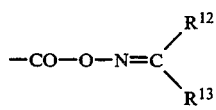

in which
$R^{12}$ has the meaning given above for $R^7$ and
$R^{13}$ has the meaning given above for $R^8$,
where, furthermore, the radical

the radicals $R^{10}$ and $R^{11}$
together represent a hydrocarbon chain which has 3 to 8 carbon atoms and which is optionally interrupted by oxygen or sulphur and in which, further, $R^9$ can also represent the same radical to which the radical —$S_q$-(O)$_r$—$R^9$ is bonded.

Carbamic esters of the formula III which are very particularly preferred as active compound components are those in which
$R^3$ represents radicals from the series comprising phenyl, naphthyl, 2,3-dihydro-7-benzofuranyl, pyrazolyl or pyrimidinyl, each of which is optionally substituted by $C_1$–$C_4$-alkyl, $C_2$–$C_4$-alkenyl, $C_1$–$C_4$-alkoxy, $C_1$–$C_4$-alkoxy-methyl, $C_1$–$C_4$-alkylthio, $C_1$–$C_4$-alkylthio-methyl, $C_1$–$C_4$-alkyl-amino, di-($C_3$–$C_4$-alkyl)-amino, di-($C_3$–$C_4$-alkenyl)-amino, halogen, dioxolanyl, methylenedioxy and/or the radical —N=CH—N(CH$_3$)$_2$, or in which
$R^3$ represents an alkylidenamino radical of the formula

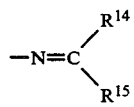

in which
$R^{14}$ and $R^{15}$ have the meaning given above for $R^7$ or $R^8$, respectively,
$R^4$ represents $C_{1-4}$-alkyl and
$R^5$ represents hydrogen or $C_1$–$C_4$-alkyl (preferably hydrogen).

Examples of the carbamic esters of the formula III which may be mentioned are the following N-methyl-carbamic esters: 2-methyl-phenyl N-methyl-carbamate, 2-ethyl-phenyl N-methyl-carbamate, 2-iso-propyl-phenyl N-methyl-carbamate, 2-sec-butyl-phenyl N-methyl-carbamate, 2-methoxy-phenyl N-methyl-carbamate, 2-ethoxy-phenyl N-methyl-carbamate, 2-iso-propoxy-phenyl N-methyl-carbamate, 4-methyl-phenyl N-methyl-carbamate, 4-ethyl-phenyl N-methyl-carbamate, 4-n-propyl-phenyl N-methyl-carbamate, 4-methoxy-phenyl N-methyl-carbamate, 4-ethoxy-phenyl N-methyl-carbamate, 4-n-propoxy-phenyl N-methyl-carbamate, 3,4,5-trimethyl-phenyl N-methyl-carbamate, 3,5-dimethyl-4-methylthio-phenyl N-methyl-carbamate, 3-methyl-4-dimethylamino-phenyl N-methyl-carbamate, 2-ethylthiomethyl-phenyl N-methyl-carbamate, 1-naphthyl N-methyl-carbamate, 2,3-dihydro-2,2-dimethyl-7-benzofuranyl N-methyl-carbamate, 2,3-(dimethyl-methylenedioxy)-phenyl N-methyl-carbamate, 2-(4,5-dimethyl-1,3-dioxolan-1-yl)-phenyl N-methyl-carbamate, 1-methylthio-ethyliden-amino N-methyl-carbamate, 2-methylthio-2-methylpropylidenamino N-methyl-carbamate, 1-(2-cyano-ethylthio)-ethylidenamino N-methyl-carbamate and 1-methylthiomethyl-2,2-dimethyl-propylidenamino N-methylcarbamate, with 2-iso-propoxy-phenyl N-methylcarbamate being preferred.

2) Carboxylic esters of the formula IV

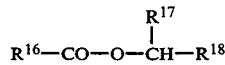

in which
$R^{16}$ represents an open-chain or cyclic alkyl radical which is optionally substituted by halogen, alkyl, cycloalkyl, by alkenyl which is optionally substituted by halogen, alkyl and/or alkoxy, by phenyl or styryl, each of which is optionally substituted by halogen, optionally halogen-substituted radicals from the series comprising alkyl, alkoxy, alkylenedioxy and/or alkylthio, by spirocyclically linked, optionally halogen-substituted cycloalk(en)yl which is optionally benzo-fused, in which furthermore
$R^{17}$ represents hydrogen, alkyl, halogenoalkyl, alkenyl, alkinyl or cyano, and
$R^{18}$ represents an optionally substituted alkyl or aryl radical, or represents a heterocycle, or, together with $R^{17}$ and the carbon atom to which both radicals are bonded, forms a cyclopentenone ring.

Carboxylic esters of the formula IV which are very particularly preferred as active compound components are those in which
$R^{16}$ represents (a) the radical

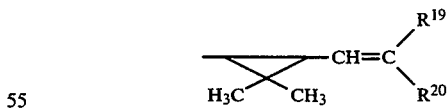

in which
$R^{19}$ represents hydrogen, methyl, fluorine, chlorine or bromine, and
$R^{20}$ represents methyl, fluorine, chlorine, bromine, $C_1$–$C_2$-fluoroalkyl or $C_1$–$C_2$-chlorofluoroalkyl, or represents phenyl which is optionally substituted by halogen and/or optionally halogen-substituted radicals from the series comprising $C_1$–$C_4$-alkyl, $C_1$–$C_4$-alkoxy, $C_1$–$C_4$-alkylthio and/or $C_1$–$C_2$-alkylenedioxy, or in which the two radicals $R^{25}$ and $R^{26}$ represent $C_2$–$C_5$-alkanediyl (alkylene);
or in which $R^{16}$ represents (b) the radical

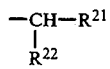

in which
$R^{21}$ represents phenyl which is optionally substituted by halogen and/or optionally halogen-substituted radicals from the series comprising $C_1$-$C_4$-alkyl, $C_1$-$C_4$-alkoxy, $C_1$-$C_4$-alkylthio or $C_1$-$C_2$-alkylenedioxy and
$R^{22}$ represents isopropyl or cyclopropyl;
or in which
$R^{16}$ represents (c) methyl or one of the radicals

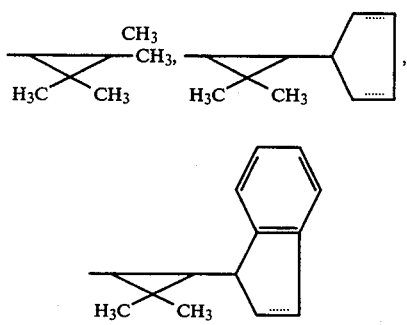

in which the dotted lines are intended to denote double bonds which are possible,
and in which
$R^{16}$ represents hydrogen, $C_1$-$C_4$-alkyl, $C_1$-$C_4$-halogenoalkyl, cyano or ethinyl and
$R^{18}$ represents radicals from the series comprising phenyl, furyl or tetrahydrophthalimido, it being possible for these radicals to be substituted by halogen and/or radicals from the series comprising $C_1$-$C_4$-alkyl, $C_2$-$C_4$-alkenyl, $C_2$-$C_4$-alkoxy, $C_1$-$C_4$-alkenoxy, $C_1$-$C_4$-alkylthio, $C_1$-$C_2$-alkylenedioxy, phenoxy and/or benzyl, all of which, in turn, can be substituted by halogen, and $R^{18}$ preferably representing tetrafluorophenyl, 3,4-dichlorophenyl, tetrahydrophthalimido, or phenoxyphenyl which can be substituted in one or in both phenyl rings by halogen (preferably fluorine).

Moreover, the naturally occurring pyrethroids (such as pyrethrum) are particularly preferred as carboxylic esters of the formula IV.

Examples which may be mentioned of carboxylic esters of the formula IV which are particularly preferred according to the invention are
3,4,5,6-tetrahydro-phthalimido-methyl 2,2-dimethyl-3-(2-methyl-propen-1-yl)-cyclopropane-carboxylate, 3-phenoxy-benzyl 2,2-dimethyl-3-(2,2-dichlorovinyl)-cyclopropane-carboxylate, α-cyano-3-phenoxy-benzyl 2,2-dimethyl-3-(2,2-dichlorovinyl)-cyclopropane-carboxylate, α-cyano-4-fluoro-3-phenoxy-benzyl 2,2-dimethyl-3-(2,2-dichlorovinyl)-cyclopropane-carboxylate, 2,3,5,6-tetrafluoro-benzyl 2,2-dimethyl-3-(2,2-dichlorovinyl)-cyclopropanecarboxylate, α-cyano-3-phenoxy-benzyl 2,2-dimethyl-3-(2,2-dibromovinyl)-cyclopropanecarboxylate and α-cyano-3-phenoxy-benzyl 3-methyl-2-(4-chlorophenyl)-butanoate.

3) Phosphoric esters and phosphonic esters of the general formula V

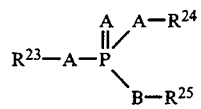

in which
A radicals are identical or different and represent O or S and
B represents O, S, —NH— or a direct bond between the central P atom and $R^{25}$ and
$R^{23}$ and $R^{24}$ are identical or different and represent optionally substituted alkyl or aryl,
$R^{25}$ represents hydrogen, optionally substituted alkyl, aryl, heteroaryl, aralkyl, alkenyl, dioxanyl or an oxime radical or the same radical to which it is bonded.

Particularly preferred phosphoric esters and phosphonic esters of the formula V are those in which
$R^{23}$ and $R^{24}$ are identical or different and represent $C_1$-$C_4$-alkyl or phenyl,
$R^{25}$ represents hydrogen, alkyl which has 1 to 4 carbon atoms and which is optionally substituted by halogen, hydroxyl, cyano, optionally halogen-substituted phenyl, carbamoyl, alkylsulphonyl, alkylsulphinyl, alkylcarbonyl, alkoxy, alkylthio, alkoxycarbonyl, alkylaminocarbonyl, the latter ones in each case having up to 6 carbon atoms, or represents alkenyl which has up to 4 carbon atoms and which is optionally substituted by halogen-substituted phenyl or $C_1$-$C_4$-alkoxycarbonyl, or represents the radical of the general formula

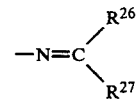

in which $R^{26}$ and $R^{27}$ have the meaning given above for $R^7$ or $R^8$, respectively, or represent cyano or phenyl, and in which
$R^{25}$ furthermore represents dioxanyl which is substituted by the same radical to which $R^{24}$ is bonded, or $R^{25}$ represents the same radical to which it is bonded, or $R^{25}$ represents phenyl which is optionally substituted by methyl, nitro, cyano, halogen and/or methylthio, and
$R^{25}$ furthermore particularly preferably represents heteroaromatic radicals such as pyridinyl, quinolinyl, quinoxalinyl, pyrimidinyl or benzo-1,2,4-triazinyl, each of which is optionally substituted by $C_1$-$C_4$-alkoxy, $C_1$-$C_4$-alkylthiomethyl, $C_1$-$C_4$-alkyl and/or halogen.

The following may be mentioned individually:
O,O-dimethyl, or O,O-diethyl, O-(2,2-dichloro-, or 2,2-dibromovinyl) phosphate,
O,O-diethyl O-(4-nitro-phenyl) thionophosphate,
O,O-dimethyl, O-(3-methyl-4-methylthio-phenyl) thionophosphate,
O,O-dimethyl O-(3-methyl-4-nitro-phenyl)thionophosphate,
O-ethyl S-n-propyl O-(2,4-dichlorophenyl) thionophosphate,
O-ethyl S-n-propyl O-(4-methylthio-phenyl) thionophosphate,
O,O-dimethyl S-(4-oxo-1,2,3-benzotriazin(3)yl-methyl) thionothiophosphate, O-methyl O-(2-iso-propyl-6-methoxy-pyrimidin(4)yl) thionomethanephosphonate, O,O-diethyl O-(2-iso-propyl-6-methyl-pyrimidin(4)yl) thionophosphate, O,O-diethyl O-(3-chloro-4-methyl-coumarin(7)yl) thionophosphate, O,O-dimethyl 2,2,2-tricloro-1-hydroxyethanephosphonate, O,O-dimethyl S-(methylaminocarbonyl-methyl) thionophosphonate.

O-methyl O-(6-methoxy-2-tert.-butyl-pyrimidin-4-yl) thionoethane-phosphonate.

4. Nitromethylene, nitromino, cyanoimino or cyanomethylene derivatives of the formula VI

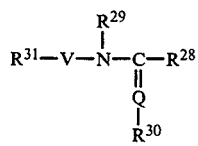

in which
R$^{28}$ represents C$_1$–C$_4$-alkyl (preferably methyl or ethyl) or the group

in which
R$^{32}$ represents C$_1$–C$_4$-alkyl (preferably methyl or ethyl) or
R$^{32}$ together with R$^{29}$ represents an optionally branched C$_2$–C$_5$-alkanediyl chain (preferably —(CH$_2$)$_2$— or —(CH$_2$)$_3$—),
and
R$^{33}$ represents hydrogen or C$_1$–C$_4$-alkyl (preferably hydrogen);
R$^{29}$ represents C$_1$–C$_4$-alkyl (preferably methyl or ethyl) or together with R$^{32}$ represents an optionally branched C$_2$–C$_5$-alkanediyl chain (preferably —(CH$_2$)$_2$— or —(CH$_2$)$_3$—),
R$^{30}$ represents NO$_2$ or CN;
R$^{31}$ represents an optionally substituted (preferably by halogen and/or C$_1$–C$_4$-alkyl) heteroaromatic radical (preferably pyridyl radical), R$^{31}$ particularly preferably representing the 2-chloropyrid-5-yl group;
Q represents =C— or =N—; and
V represents a direct bond or a C$_1$–C$_3$-alkanediyl radical (preferably —CH$_2$—).

In what follows, some particularly preferred compounds of the formula VI are mentioned specifically by way of example:

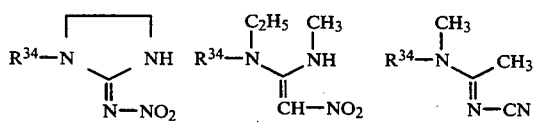

in which R$^{34}$ represents the

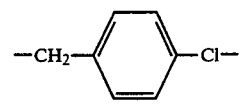

radical.

Depending on their particular physical and/or chemical properties, the compounds of the formula I and/or the insecticidal substances and the mixtures of the compounds of the formula I with the insecticidal substances can be converted to the customary formulations, such as solutions, emulsions, suspensions, powders, foams, pastes, granules, aerosols, natural and synthetic materials impregnated with active compound and very fine capsules in polymeric substances.

These formulations are produced in a known manner, for example by mixing the active compounds with auxiliaries and/or extenders, that is, liquid solvents, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformide and dimethyl sulphoxide, as well as water; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

When formulated as baits (preferably bait formulations for scattering or solid bait formulations), the formulations can additionally contain other additives which attract the cockroaches and/or encourage them to ingest the insecticidal substances. Attractants and edible substances which can be used are all preparations which are conventionally used, such as natural or synthetic odoriferous substances, colourants and/or substances which are pallatable to cockroaches, such as starch-containing and/or sugar-containing products based on cereals.

The formulations preferably contain 0.001 to 95, in particular 0.01 to 70, per cent by weight of compounds of the formula I.

The formulations of the insecticidal substances contain preferably between 0.1 and 95, in particular 0.5 and 90, per cent by weight of insecticidal substances (if appropriate besides the compounds of formula I).

The agents for combating cockroaches are applied in customary manner adapted to suit the use form.

The biological activity of the compounds of the formula I will be illustrated with the aid of the examples below.

A) Improved Activity of a Bait Formulation

In a room (2.25×4.70 m) there are, in two opposite corners, in each case a hiding place and a drinking place, and, in the two other corners, in each case a piece of rusk. One day after 20 male and 20 female cockroaches (*Blattella germanica*) have been released, in each case one bait container with an insecticide-containing edible tablet (in the present case 0.5% of ethylchlorpyrifos) is placed at a distance of 40 cm to the rusk.

On the inside of the lid of the bait container, there is a platelet which had been treated 1 hour earlier with a compound of the formula I (dissolved in n-hexane) or only with n-hexane (untreated bait=control).

Treated bait containers and untreated bait containers were placed in each case in 3 rooms.

The next day, the mortality of the male and female animals was determined.

The test results can be seen from Table 2 which follows:

TABLE 2

| Test compound of TABLE 1 | Mortality in % after 1 day (mean value of 3 experiments) | |
|---|---|---|
| | male cockroaches | female cockroaches |
| 1 | 47 | 48 |
| control | 42 | 37 |
| 2 | 38 | 28 |
| control | 27 | 25 |
| 3 | 78 | 62 |
| control | 25 | 33 |
| 4 | 53 | 54 |
| control | 33 | 29 |

B) Improving the Activity of a Spray Preparation

Ceramic tiles are sprayed with an aqueous spray mixture containing (a) a formulation containing 50 g of cyfluthrin/liter and (b) this formulation and additionally the Compound 3 of Table 1. The application rate of cyfluthrin is in each case 20 mg/active compound per m² of tile. The application rate of Compound No.3 is 4 mg of active compound per m² of tile.

In each case one of these tiles is placed in the corner of a container (49×59 cm, height 29.5 cm) in which there are a drinking place, feed, a hiding place, as well as males and females of *Blattella germanica* which have been introduced 2 hours before (in each case 5). Each experiment consists of 3 replications. The mortality is determined after 1, 2 and 3 days, and the mean value of the 3 experiments is calculated.

Test results:

| Tiles treated with (active compound/m²) | Mortality in % after | | |
|---|---|---|---|
| | 1 day | 2 days | 3 days |
| 20 mg of cyfluthrin + 4 mg of Compound No. 3 of TABLE 1 | 70 | 90 | 93 |
| 20 mg of cyfluthrin (control) | 43 | 70 | 70 |

The preparation of the compounds of the general formula I shall now be illustrated with the aid of the examples below:

EXAMPLE 1

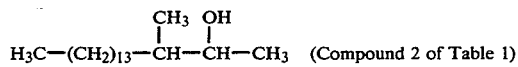
(Compound 2 of Table 1)

2 g (7.46 mmol) of 3-methyl-heptadecan-2-one are dissolved in 20 ml of ethanol and the solution is treated, at 0° C., with 0.28 g (7.46 mmol) of sodium borohydride. Stirring is continued for two hours at 0° C. and for two hours at room temperature. The mixture is subsequently concentrated under reduced pressure, the concentrate is taken up in cyclohexane/water, and the aqueous phase is extracted three times using cyclohexane. After the extract has been dried and concentrated, 2 g (99% of theory) of 3-methyl-heptadecan-2-ol are obtained as pure substance.

$^1$H NMR (200 MHz, CDCl$_3$): $\delta$=0.9 (2d, 6H), 1.18 (t, 3H), 1.2–1.6 (m, 27H), 3.65 (m, 1H)

Compound No. 1 of Table 1 is synthesised analogously:

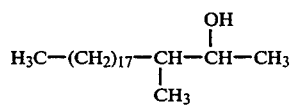

$^1$H NMR (200 MHz, CDCl$_3$): $\delta$=0.88 (d+t, 6H), 1.15 (t, 3H), 1.20–1.40 (m, 35 H), 3.60–3.75 (m, 1H).

EXAMPLE 2

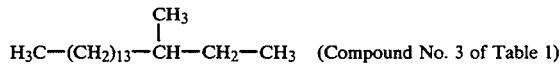
(Compound No. 3 of Table 1)

2 g (7.46 mmol) of 3-methyl-heptadecan-2-one (Compound No. 3 of Table 1) are introduced into 10 ml of diethylene glycol, and the mixture is treated with 1.11 g (22.4 mmol) of hydrazine hydrate and 1.2 g (29.85 mmol) of sodium hydroxide. The mixture is stirred for twenty hours at 200° C. When the mixture has cooled to room temperature, it is treated with 100 ml of water, acidified with hydrochloric acid, with cooling, and extracted three times using cyclohexane. The combined organic extracts are washed twice with a little water, dried over sodium sulphate and concentrated. Separation by column chromatography using cyclohexane as the eluent gave 1.0 g (53% of theory) of 3-methylheptadecane.

MS m/z (%): 254 (23, M+),225 (46), 196 (18), 155 (17), 113 (22), 99 (28), 85 (67), 71 (83), 57 (100).

Compound No.4 of Table 1 is also synthesised analogously to this procedure

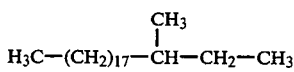

$^1$H NMR (200 MHz, CCl$_3$): δ=0.85 (6, 9H), 1.1–1.4 (m, 37H).

The starting compounds can be synthesised by known preparation methods (cf. Agr. Biol. Chem. 40, 391 (1976); J. Org. Chem. 42, 566 (1977).

What is claimed is:

1. A mechanical device for combating cockroaches, containing at least one compound of the formula

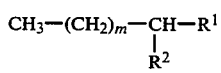   I in which
R$^1$ represents C$_1$–C$_5$-alkyl or hydroxy-C$_1$–C$_5$-alkyl;
R$^2$ represents C$_1$–C$_5$-alkyl and
m represents an integer from 10 to 20, 2. A device according to claim 1, wherein
R$^1$ represents C$_1$–C$_4$-alkyl or hydroxy-C$_1$–C$_4$-alkyl,
R$^2$ represents C$_1$–C$_3$-alkyl; and
m represents an integer from 11 to 19.

3. A device according to claim 1, wherein
R$^1$ represents C$_1$–C$_3$-alkyl or hydroxy-C$_1$–C$_3$-alkyl;
R$^2$ represents methyl or ethyl and
m represents an integer from 12 to 18.

4. A device according to claim 1, wherein
R$^1$ represents hydroxy-C$_1$–C$_5$-alkyl;
R$^2$ represents C$_1$–C$_5$-alkyl; and
m represents an integer from 10 to 20.

5. A device according to claim 1, further containing at least one entomopathogenic virus or microorganism and/or at least one insecticidally active substance and one or more auxiliaries and/or extenders and/or other additives,
it being possible for the components to exist in the form of a mixture or as a separate arrangement.

6. An agent for combating cockroaches, having a tacky surface to which cockroaches adhere and which in the tacky surface or adjacent thereto contains at least one compound of the formula

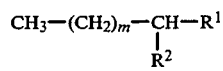   I in which
R$^1$ represents C–C$_5$-alkyl or hydroxy-C$_1$–C$_5$-alkyl;
R$^2$ represents C$_1$–C$_5$-alkyl; and
m represents an integer from 10 to 20.

7. An agent according to claim 6, wherein
R$^1$ represents C$_1$–C$_4$-alkyl or hydroxy-C$_1$–C$_4$-alkyl,
R$^2$ represents C$_1$–C$_3$-alkyl; and
m represents an integer from 11 to 19.

8. A device according to claim 1, wherein
R$^1$ represents C$_1$–C$_3$-alkyl or hydroxy-C$_1$–C$_3$-alkyl;
R$^2$ represents methyl or ethyl; and
m represents an integer from 12 to 18.

9. A device according to claim 1, wherein
R$^1$ represents hydroxy-C$_1$–C$_5$-alkyl;
R$^2$ represents C$_1$–C$_5$-alkyl; and
m represents an integer from 10 to 20 .

10. In the killing of cockroaches employing an agent for combating cockroaches and a cockroach attractant, the improvement wherein said attractant comprises at least one compound of the formula

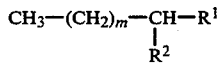   I in which
R$^1$ represents C$_1$–C$_5$-alkyl or hydroxy-C$_1$–C$_5$-alkyl;
R$^2$ represents C$_1$–C$_5$-alkyl; and
m represents an integer from 10 to 20.

* * * * *

UNITED STATES PATENT AND TRADEMARK OFFICE
CERTIFICATE OF CORRECTION

PATENT NO. : 5,365,691
DATED : November 22, 1994
INVENTOR(S) : Scherkenbeck, et al.

It is certified that error appears in the above-indentified patent and that said Letters Patent is hereby corrected as shown below:

Col. 16, line 15  Delete " $C-C_5$-alkyl " and substitute -- $C_1-C_5$-alkyl --

Signed and Sealed this

Second Day of December, 1997

Attest:

BRUCE LEHMAN

Attesting Officer     Commissioner of Patents and Trademarks